(12) United States Patent
Chow et al.

(10) Patent No.: US 7,572,939 B2
(45) Date of Patent: Aug. 11, 2009

(54) TYPE OF SOLUBLE PENTACENE PRECURSOR

(75) Inventors: Tahsin J. Chow, Taipei (TW); Kew-Yu Chen, Taoyuan (TW); Jiunn-Jye Hwang, Taipei (TW)

(73) Assignee: Academia Sinica, Nankang, Taipei (TW)

( * ) Notice: Subject to any disclaimer, the term of this patent is extended or adjusted under 35 U.S.C. 154(b) by 701 days.

(21) Appl. No.: 11/351,399

(22) Filed: Feb. 10, 2006

(65) Prior Publication Data

US 2007/0190254 A1    Aug. 16, 2007

(51) Int. Cl.
C07C 49/00    (2006.01)
C07C 15/00    (2006.01)
B05D 3/02    (2006.01)

(52) U.S. Cl. .................. 568/367; 585/400; 427/372.2

(58) Field of Classification Search ................ None
See application file for complete search history.

(56) References Cited

U.S. PATENT DOCUMENTS

| | | |
|---|---|---|
| 6,963,080 B2 | 11/2005 | Afzali-Ardakani et al. |
| 2003/0136964 A1 | 7/2003 | Afzali-Ardakani et al. |
| 2003/0144562 A1 | 7/2003 | Afzali-Ardakani et al. |
| 2004/0119073 A1 | 6/2004 | Ardakani et al. |

FOREIGN PATENT DOCUMENTS

| | | |
|---|---|---|
| CN | 1585151 | 2/2005 |
| WO | WO 2004/083160 | 9/2004 |

OTHER PUBLICATIONS

Lai et al. Theoretical Investigation of Cheletropic Decarbonylation Reactions. Journal of Chemical Theory and Computation, 2006, vol. 2, p. 1078-1084.*

A Soluble Pentacene Precursor: Synthesis, Solid-State Conversion into Pentacene and Application in a Field-Effect Transistor, Peter T. Herwig and Klaus Müllen, Advanced Materials, Dec. 23, 1998.
Robust, Soluble Pentacene Ethers, Marcia M. Payne, et al. Organic Letters, 2004, vol. 6, No. 102 1609-1612.
A Photopatternable Pentacene Precursor for Use in Organic Thin-Film Transistors, Kevin P. Weidkamp, et. al., J A C S Communications, J.AM. Chem. Soc. 2004, 126, 12740-12741.
New Soluble Pentacene Precursors for the Application of Organic Thin-Film Transistors, Meyoung Ju Joung, et al. Bull. Korean Chem. Soc. 2003, vol. 24, No. 12.
Photochemical Synthesis of Pentacene and its Derivatives, Hiroko Yamada, et al., Chem. Eur. J. 2005, 11, 6212-6220.
High Performance, Solution-Processed Organic Thin Film Transistors from a Novel Pentacene Precursor, Ali Afzali, et al., J.AM. Chem. Soc. 2002, 124, 8812-8813.
Photo Precursor for Pentacene, Hidemitsu Uno, et al., Elsevier, Tetrahedron Letters 46 (2005) 1981-1983.
7-*t*-Butoxynorbornadiene [2,5-Norbornadiene, 7-tert-butoxy-], Paul R. Story, et al., Organic Synthesis, Coll. vol. 5, p. 151 (1973); vol. 44, p. 12 (1964).
Inkjetted Organic Transistors using a Novel Pentacene Precursor, Steven K. Volkman, et al., Mat. Res. Soc. Symp. Proc., 2003 Materials Research Society.

* cited by examiner

*Primary Examiner*—Sikarl A Witherspoon
(74) *Attorney, Agent, or Firm*—Cohen Pontani Lieberman & Pavane LLP

(57) ABSTRACT

A novel soluble pentacene ($C_{22}H_{14}$) precursor 6,13-dihydro-6,13-methanopentacene-15-one, a method for its production and intermediates therefor as well as pentacene films and coated surfaces. Thermolysis of the precursor at 150° C. to 350° C. induces an expulsion of carbon monoxide to generate pentacene in high yield. The high solubility of the precursor compound, as well as its production of non-contaminated pentacene, makes it an excellent material in the application of organic thin film transistors on surfaces.

19 Claims, 3 Drawing Sheets

TYPE OF SOLUBLE PENTACENE PRECURSOR

BACKGROUND OF THE INVENTION

1. Field of the Invention

The present invention is in a novel soluble pentacene precursor, an intermediate for the precursor, a method for the preparation of the precursor and products resulting from use of the new precursor.

2. Description of the Related Art

It is widely recognized that pentacene ($C_{22}H_{14}$) is a preferred organic semiconducting material for the fabrication of organic thin film transistors (OTFT) due to its high electron mobility, improved on-off ratio, improved environmental stability and better reliability than most other organic semiconductors. Pentacene is recognized as a viable alternative to inorganic thin films based on Si or Ge for transistor applications. A major drawback to using pentacene is that the compound has a low solubility in most solvents. The lack of a suitable solvent not only makes the purification of pentacene difficult but also necessitates the use of difficult procedures, such as vapor phase deposition under high vacuum, in order to cast a film on a TFT device.

Considerable effort has been devoted in an attempt to prepare "soluble" pentacene precursors in order to overcome this problem. The availability of a soluble material would facilitate the preparation of solid films through one or more of the known operations of spin-coating, spray coating, screen printing or inkjet printing. Of course, the precursor must be soluble in solvents which are commercially permissible.

Several pentacene precursors have been reported. Most of the reported precursors are cyclic adducts of pentacene and another minor fragment. One such cyclic adduct is shown in U.S. Pat. No. 6,963,080. The adduct is produced by way of a Diels-Alder reaction using, inter alia, N-sulfinyamides as the dienophile. But such compounds can be difficult to work with.

Solid films of large size can be prepared by spin-coating the precursor solutions. After the films are dried, a chemical reaction is triggered either by heat or by light to expel the volatile minor fragment. Subsequently, the resulting films of pure pentacene are annealed at a proper temperature for self-reorganizing of their morphology, which is crucial for promoting their charge mobility.

SUMMARY OF THE INVENTION

The present invention is in a new and improved soluble pentacene precursor. The new precursor is 6,13-dihydro-6,13-methanopentacene-1,5-one.

In another aspect of the invention, intermediate compounds to the precursor are disclosed.

The invention also includes a method of making the precursor and/or intermediate compounds therefor.

Another aspect of the invention includes products made with the precursor which can include thin films and thin film coated surfaces.

The various features of novelty which characterize the invention are pointed out with particularity in the claims annexed to and forming a part of the disclosure. For a better understanding of the invention, its operating advantages, and specific objects attained by its use, reference should be had to the drawings and descriptive matter in which there are illustrated and described a preferred embodiment of the invention.

DETAILED DESCRIPTION OF THE PRESENTLY PREFERRED EMBODIMENTS

The present invention is in a novel pentacene precursor which is soluble, a method for making the soluble precursor, intermediates for the precursor and a product of the soluble precursor such as a thin film and a thin film coated surface.

The novel precursor is 6,13-dihydro-6,13-methanopentacene-1,5-one having the structure (Compound 3) shown in the below schematic. The novel precursor can be produced by a simple three step process schematically depicted below using a 7-substituted norbornadiene as a starting material. 7-t-butoxynorbornadiene can be prepared from norborndiene and cuprous bromide in benzene in an inert atmosphere.

The novel pentacene precursor compound is stable at ambient conditions, and can be prepared readily from 7-tert-butoxynorbornadiene in a total yield of about 27%. The soluble precursor can then be dissolved or readily dispersed into an appropriate solvent and applied by known techniques to a surface. Carbon monoxide (CO) is expelled from the novel precursor to produce pentacene in high yield at moderate temperatures.

The synthesis of the novel precursor by a preferred method is schematically depicted below. The first step of the method of the invention requires a double annulation (double annellation) of two naphthalene moieties onto the C=C bonds of 7-tert-butoxynorbornadiene. The double annulation is accomplished by reacting the substituted norbornadiene with α,α,α',α'-tetrabromo-o-xylene. The annulation reaction is carried out by reacting the starting materials in the presence of a suitable salt, preferably sodium iodide, in a solvent such as N,N-Dimethyl-Formamide ("DMF"). The reaction is conducted at about 65° C. The result of the reaction is a first intermediate designated as Compound (1) in the below schematic. Of course, Compound (1) can be obtained by other routes and can be used as the starting material in a simplified two step process.

In the next step of the preferred method, Compound (1) is treated with a hydrolysis agent hydrolyzing the tert-butoxy group of Compound (1) to a hydroxyl group to form Compound (2). A preferred hydrolysis agent is $H_sSO_4$ and in particular concentrated sulfuric acid diluted with water to 50% of its concentration, i.e. 1 volume of concentrated $H_2SO_4$ diluted to twice its volume In the next step of the process, Compound (2) is subjected to oxidation by an oxidizing agent to form Compound (3) which is the novel precursor. In a preferred embodiment, the oxidation is conducted with a sulfur trioxide/pyridine complex at ambient temperature in DMSO. The preferred complex has a 1:1 ratio of sulfurtrioxide to pyridine. Such a complex is available from Tokyo Kasai Kogyo, Co. Ltd of Japan. Other oxidizing agents include PCC (pyridium chlorochromate) and PDC (pyridium dichromate). Compound (3) exhibits a $C_{2v}$ symmetry as indicated by the presence of four $^1$H NMR signals in a ratio of 2:2:2:1. A strong absorption at 1778 cm$^{-1}$ in IR confirms the presence of a carbonyl group.

Figure 2:
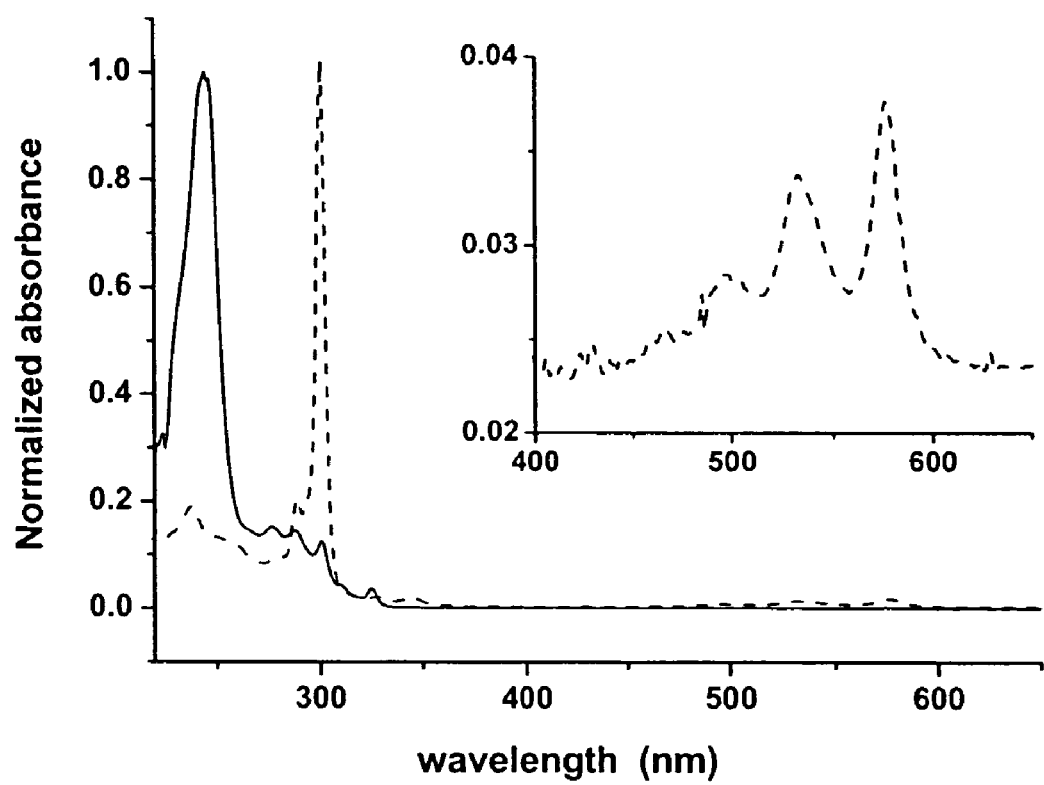
FIG. 2 shows a UV-Vis spectra of the novel precursor (solid line) and the thermal-converted pentacene (dotted line) in dichloromethane. The inset magnifies the weak bands in the region of 400–600 nm, which is characteristic for pentacene.

FIG. 2 shows a UV-Vis spectra of the novel precursor (solid line) and the thermal-converted pentacene (dotted line) in dichloromethane. The inset magnifies the weak bands in the region of 400~600 nm, which is characteristic for pentacene. In the infra-red spectra, the strong absorption peak at 1778 cm$^{-1}$, corresponding to the carbonyl stretching of Compound

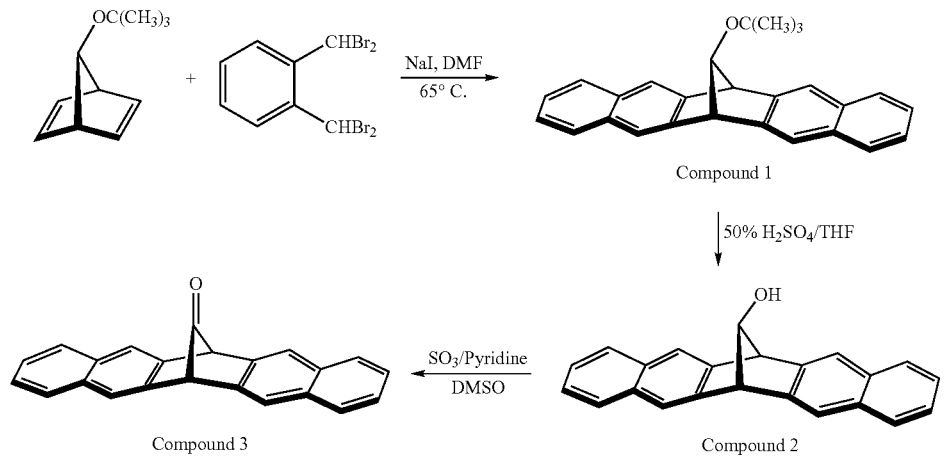

Compound 3 is quite soluble in dichloromethane benzene, toluene, acetone, and tetrahydrofuran (all in the range of ~2.0 mM i.e. about 0.7 mg/mL solvent) but is not soluble in methanol, ethanol, or acetonitrile. Compound (3) can be applied to a surface of an article by spin coating, spray coating, screen printing or ink-jet printing to form a film. The film can be dried in any of the conventional ways including air drying or with mild heating, i.e. below about 120° C. Subsequent to drying, a chemical reaction is initiated preferably by the application of heat resulting, inter alia, in the driving off of volatile components including CO.

Figure 1:
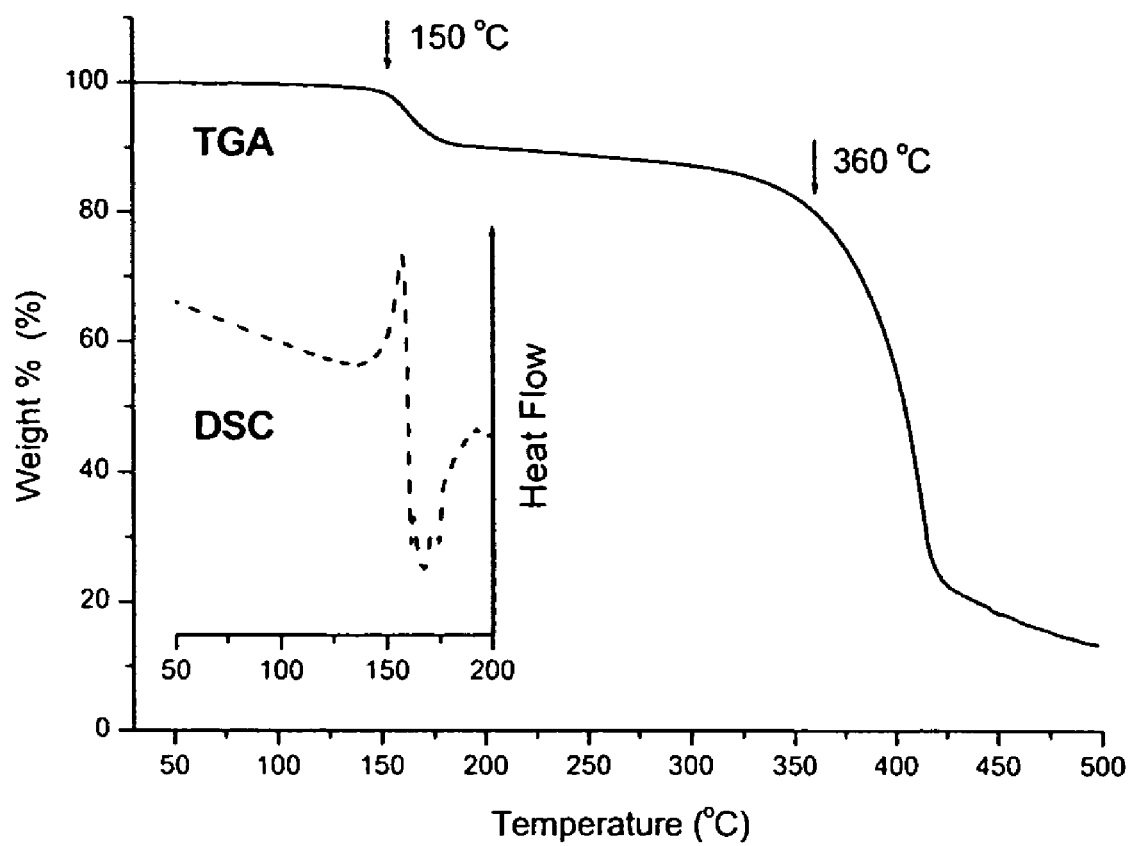
FIG. 1 shows a thermogravimetric curve for the decarbonylation of the novel precursor at 10° C./min heating rate. The inset at the bottom shows a curve of differential scanning calorimetry, also at 10° C./min.

Thermal initiated carbonyl extrusion can be depicted by both TGA (thermal gravimetric analysis) and DSC (differential scanning calorimetry) studies. As shown in FIG. 1, Compound (3) undergoes a fragmentation at 150° C. FIG. 1 shows a thermogravimetric curve for the decarbonylation of the novel precursor at 10° C./min heating rate. The inset at the bottom shows a curve of differential scanning calorimetry, also at 10° C./min. The decarbonylation appears at 150° C. to yield pentacene, which decomposes at about 360° C. as measured by 5% weight loss. During the extrusion, Compound (3) loses about 9% weight corresponding to the weight ratio of CO in the molecule. The pentacene thus produced is stable up to temperatures of about 350° C. Above about 350° C., Compound (3) starts to experience thermal decomposition.

The thermal transformation is characterized by UV spectra before and after the heating. Two low energy absorption bands of Compound (3) appear at 301 and 326 nm, which exhibit fine vibronic progressions (FIG. 2). This band is analogous to that of naphthalene, as the structure of Compound (3) includes two naphthalene units. A much stronger absorption band is observed at 244 nm. After heating at 160° C. for about 1 hour, this absorption band disappears completely, while another strong peak arises at 300 nm. The two low energy bands red-shifted to 346 and 576 nm as a result of more extended π-conjugation in pentacene. The spectrum of the thermal product is consistent with that of authentic pentacene.

Figure 3:
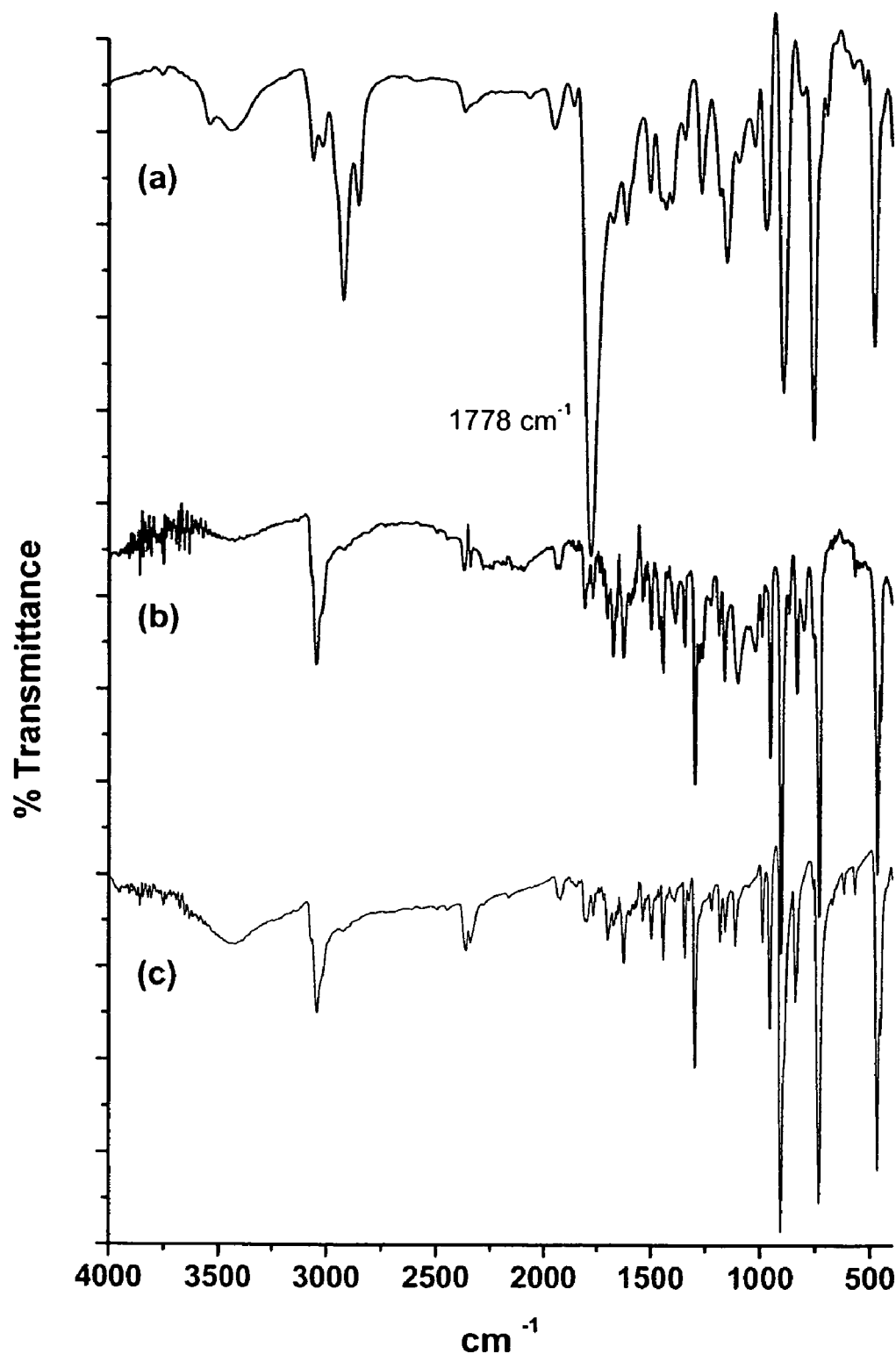
FIG. 3 shows the Infrared spectra of the novel precursor (a) before and (b) after heating at 160° C. for 1 h. and includes a standard infrared spectrum of commercial pentacene (c) presented at the bottom for comparison.

(3), disappears upon heating (FIG. 3). A clear transformation of Compound (3) to pure pentacene is thus demonstrated.

EXAMPLE

General: $^1$H$^{13}$C NMR spectra were obtained on a Bruker AMX-400 spectrometer. Infrared spectra were recorded on a Perkin-Elmer 682 infrared spectrophotometer. Ultraviolet-visible absorption Spectra were recorded on a HP 8453 spectrophotometer. Differential scanning calorimetry was done on a Perkin-Elmer model DSC7 instrument. Thermal gravimetric analysis was performed by a Perkin-Elmer TGA7 analyzer.

6,13-dihydro-6,13-methano-15-tert-butoxypentacene (Compound 1)

A solution of α,α,α'α'-tetrabromo-o-xylene (5.0 g, 12 mmol), 7-t-butoxynorbornadiene (1.00 g, 6.0 mmol), sodium iodide (5.4 g, 36 mmol) was prepared in dry DMF (50 mL) and was stirred at 65° C. for 24 hours. The reaction was quenched by pouring into cold water (100 mL) containing sodium bisulfite (5.0 g). Brown precipitates were collected, and were purified by silica-gel column chromatography eluted with hexane: ethyl acetate (v/v=20/1) to give Compound 1 (1.2 g) in 55% yield. $^1$H NMR (400 MHz, CDCl$_3$) δ7.73(m, 8H), 7.38 (m, 4H), 4.45 (s, 2H), 4.41 (s, 1H), 1.17 (s, 9H).

6,13-dihydro-6,13-methano-15-hydroxypentacene (Compound 2)

Compound 1 (1.00 g, 2.7 mmol) was added to a solvent which is a mixture of tetrahydrofuran (20 mL) and 50% aqueous sulfuric acid (10 mL). The mixture was stirred at room temperature for 48 hr. It was quenched by the addition of distilled water, and was extracted by ether. The combined ether layers were washed with brine, and dried over anhydrous magnesium sulfate. The organic solvent was removed in vacuo, and the product was purified by silica-gel chromatography eluted with hexane:ethyl acetate (v/v=4/1) to give Compound 2 (0.70 g) in 83% yield. $^1$H NMR (400 MHz, CDCl$_3$) δ7.85 (s, 2H), 7.74 (m, 6H), 7.42 (m, 4H), 4.59 (s, 1H), 4.52 (s, 2H), 2.30 (br, 1H).

6,13-dihydro-6,13-methanopentacene-15-one
(Compound 3)

To a solution of Compound 2 (0.50 g, 1.6 mmol) in 10 mL of dichloromethane were added dimethyl sulfoxide (5 mL) and triethylamine (0.60 g, 6.0 mmol). To the resulting solution a solution of sulfur trioxide/pyridine complex (0.70 g, 4.4 mmol) in dimethyl sulfoxide (9 mL) was added drop-wise over a 30 minute period. The mixture was stirred at room temperature for 12 hr. The reaction was quenched by pouring into saturated aqueous NH$_4$Cl (50 mL). It was extracted several times with CH$_2$Cl$_2$. The combined phase washed with brine, dried over anhydrous magnesium sulfate, and dried in vacuo. The product was purified by silica-gel column chromatograph eluted with hexane:ethyl acetate (v/v=4/1) to give Compound 3 (0.30 g) in 60% yield. $^1$H NMR (400 MHz, CDCl$_3$) δ7.92(s, 4H), 7.81 (dd, J=3.3, 6.2 Hz, 4H), 7.46 (dd, J=3.2, 6.2 Hz, 4H), 4.98 (s, 2H). IR (KBr) 3063, 2922, 1778, 1609, 1500, 893, 757 cm$^{-1}$.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:
1. A compound 6,13-dihydro-6, 13-methanopentacene-15-one.
2. A compound 6,13-dihydro-6,13-methano-15-hydroxypentacene.
3. A compound 6,1 3-dihydro-6, 13-methano-15-tert-butoxypentacene.
4. A method of forming pentacene comprising initiating a chemical reaction of 6,13-dihydro-6,13 methanopentacene-1 5-one to form pentacene.
5. The method of claim 4 wherein the chemical reaction is initiated by heat.
6. The method of claim 5 wherein the chemical reaction is initiated by a thermolysis at a temperature of from about 150° C. to about 350° C.
7. A method of forming pentacene on a surface comprising:
applying 6,13-dihydro-6,13-methanopentacene-15-one to the surface;
subjecting the 6,13-dihydro-6,13-methanopentacene-15-one to a thermolysis at a temperature of from about 150° C. to 350° C. so as to cause fragmentation of the 6,13-dihydro-6,13-methanopentacene-15-one to form pentacene on said surface.
8. The method of claim 7 wherein the 6,13-dihydro-6,13-methanopentacene-15-one is applied as a film or coating on the surface.
9. The method of claim 8 wherein the film or coating is applied to the surface by spin-coating, spray coating, screen printing or ink-jet printing.
10. The method of claim 8 wherein the film is dried prior to the thermolysis.
11. The method of claim 10 wherein the film is dried by air drying or the application of mild heat.
12. The method of claim 10 wherein CO is given off during the thermolysis.
13. A method of producing 6,13-dihvdro-6,13-methanonentacene-15-one comprising:
oxidizing 6,13-dihydro-6,13-methano-15-hydroxypentacene to form the soluble pentacene precursor 6,13-dihydro-6,13-methanopentacene-15-one.
14. The method of claim 13 wherein the 6,13-dihydro-6, 13-methano-15-hydroxypentacene is formed by the hydrolysis of 6,13-dihydro-6, 13-methano-15-tert-butoxypentacene.
15. The method of claim 14 wherein the hydrolysis is with sulfuric acid.
16. The method of claim 13 wherein the step of oxidizing is by use of an oxidizing agent selected from the group consisting of a sulfurtrioxide containing complex, pyridinium chlorochromate, pyridinium dichromate and mixtures thereof.
17. The method of claim 16 wherein the sulfurtrioxide containing complex is sulfurtrioxide/pyridine.
18. A method of forming a pentacene film on a substrate comprising:
applying a film of 6,13-dihydro-6, 13-methanopentacene-15-one to the substrate by spin coating, spray coating, screen printing or inkjet printing; and initiating a chemical reaction of the 6,13-dihydro-6,13-methanopentacene-15-one to form pentacene.
19. A method of forming a thin film transistor, said method comprising thermolysis of 6,13-dihydro-6,13-methanopentacene-1 5-one.

* * * * *